United States Patent
Keränen

(10) Patent No.: US 10,765,516 B2
(45) Date of Patent: Sep. 8, 2020

(54) DEVICE AND METHOD FOR IMPROVING THE FUNCTION OF A HEART VALVE

(71) Applicant: Medtentia International Ltd., Oy, Helsinki (FI)

(72) Inventor: Olli Keränen, Bjärred (SE)

(73) Assignee: Medtentia International Ltd., Oy, Helsinki (FI)

( * ) Notice: Subject to any disclaimer, the term of this patent is extended or adjusted under 35 U.S.C. 154(b) by 0 days.

(21) Appl. No.: 16/246,374

(22) Filed: Jan. 11, 2019

(65) Prior Publication Data

US 2019/0183646 A1 Jun. 20, 2019

Related U.S. Application Data

(63) Continuation of application No. 11/793,028, filed as application No. PCT/SE2005/001914 on Dec. 14, 2005, now Pat. No. 10,201,424.

(60) Provisional application No. 60/636,096, filed on Dec. 16, 2004.

(30) Foreign Application Priority Data

Dec. 15, 2004 (SE) ...................................... 0403046

(51) Int. Cl.
*A61F 2/24* (2006.01)

(52) U.S. Cl.
CPC .... *A61F 2/2445* (2013.01); *A61F 2220/0008* (2013.01); *A61F 2250/0007* (2013.01)

(58) Field of Classification Search
CPC ....................................................... A61F 2/24
See application file for complete search history.

(56) References Cited

U.S. PATENT DOCUMENTS

| 6,217,610 B1 | 4/2001 | Carpentier et al. |
| 6,602,289 B1 | 8/2003 | Colvin et al. |
| 6,723,038 B1 | 4/2004 | Schroeder et al. |
| 2001/0021874 A1 | 9/2001 | Carpentier et al. |
| 2004/0127981 A1 | 7/2004 | Rahdert et al. |
| 2004/0127982 A1 | 7/2004 | Machold et al. |

(Continued)

FOREIGN PATENT DOCUMENTS

WO  WO99/04730 A1  2/1999

OTHER PUBLICATIONS

WIPO, Swedish International Preliminary Examining Authority, International Preliminary Report on Patentability dated Jun. 19, 2007 in International Patent Application No. PCT/SE2005/001914, 7 pages.

*Primary Examiner* — Matthew W Schall
(74) *Attorney, Agent, or Firm* — Inskeep IP Group, Inc.

(57) ABSTRACT

A device for improving the function of a heart valve has a first and a second shape. The device comprises two contact points, wherein the device in the first shape exhibits a distance between the two contact points essentially corresponding to a distance between two commissures of the heart valve and the device in the second shape exhibits an increased distance between the contact points. The device is in the first shape arranged for insertion to the heart valve to establish a contact between the contact points and the commissures. The device is transferable from said first shape to said second shape, and the device is in the second shape arranged for extending in abutment with valve tissue throughout a cycle of heart action. The device may change the shape of the heart valve by stretching it between the commissures for improving the ability of the heart valve to close.

20 Claims, 10 Drawing Sheets

(56) References Cited

U.S. PATENT DOCUMENTS

2004/0220593 A1 11/2004 Greenhalgh
2004/0236419 A1 11/2004 Milo
2004/0260393 A1 12/2004 Rahdert et al.

DEVICE AND METHOD FOR IMPROVING THE FUNCTION OF A HEART VALVE

RELATED APPLICATIONS

This application is a continuation of U.S. patent application Ser. No. 11/793,028 filed Jun. 14, 2007 entitled Device And Method For Improving The Function Of A Heart Valve, which is the U.S. National Phase of and claims priority to International Patent Application No. PCT/SE2005/001914, International Filing Date Dec. 14, 2005, entitled A Device And Method For Improving The Function Of A Heart Valve, which claims benefit of and priority to U.S. Provisional Application Ser. No. 60/636,096 filed Dec. 16, 2004 and Swedish Application No. 0403046-6 filed Dec. 15, 2004, all of which are hereby incorporated herein by reference in their entireties.

FIELD OF THE INVENTION

The present invention generally relates to improving the function of a heart valve. More specifically, the invention relates to a device and a method for treating heart valves having various malformations and dysfunctions.

BACKGROUND OF THE INVENTION

Diseased mitral and tricuspid valves frequently need replacement or repair. The mitral and tricuspid valve leaflets or supporting chordae may degenerate and weaken or the annulus may dilate leading to valve leak (insufficiency). The leaflets and chords may become calcified and thickened rendering them stenotic (obstructing forward flow). Finally, the valve relies on insertion of the chordae inside the ventricle. If the ventricle changes in shape, the valve support may become non-functional and the valve may leak.

In valve repair, a diseased valve is left in situ and surgical procedures are performed to restore its function. There are numerous approaches for repairing a heart valve in order to restore or improve its function. Frequently an annuloplasty ring is used to reduce the size of the annulus. The ring serves to reduce the diameter of the annulus and allow the leaflets to oppose each other normally. Sutures are used to attach a prosthetic ring to the annulus and to assist in plicating the annulus.

According to another method, the leaflets are attached to each other at free edges of the leaflets by means of sewing or a clip. This implies that two orifices are created, one on each side of the attachment of the leaflets. These double orifices may then close properly.

An example of a clip for attaching the leaflets to each other is disclosed in US 2004/0220593.

In U.S. Pat. No. 6,723,038, there is disclosed devices for improving mitral valve function. One device comprises a splint for improving the function of a valve of a heart. The splint includes an elongate member configured to be positioned transverse a heart chamber so that each end of the elongate member extends through a wall of the heart, and first and second anchoring members configured to be positioned external the chamber and attached to the ends of the elongate member to fix the elongate member in a position across the chamber. The first anchoring member includes a first portion configured to contact a first region of the heart proximate the valve annulus to change a shape of the valve annulus by compressing the heart. The change of shape of the valve annulus helps restoring the heart function. However, using this device, the elongate member will be placed in the blood flow and therefore the patient will need lifelong anti-thrombosis treatment in order to prevent blood clots forming within the blood flow.

SUMMARY OF THE INVENTION

It is an object of the invention to provide a more easily accomplished valve repair to provide improved heart valve function. It is a specific object of the invention to accomplish a valve repair that does not interfere with the blood flow through the heart valve.

These and other objects of the invention are accomplished by means of a device and a method according to the independent claims. Preferred embodiments of the invention are apparent from the dependent claims.

Thus, there is provided a device for improving the function of a heart valve comprised of valve tissue including an annulus, leaflets and at least a first and a second commissure between adjacent leaflets. The device has a first shape and a second shape and comprises a first contact point and a second contact point, wherein the device in the first shape exhibits a distance between the first contact point and the second contact point essentially corresponding to a distance between said first and second commissure of the heart valve and the device in the second shape exhibits an increased distance between the first and the second contact points. In the first shape, the device is arranged for insertion to the heart valve to establish a contact between the first contact point and valve tissue at the first commissure and to establish a contact between the second contact point and valve tissue at the second commissure. The device is transferable from said first shape to said second shape when inserted to the heart valve, and, in the second shape, the device is arranged for extending along substantially its entire length between the first contact point and the second contact point in abutment with valve tissue throughout a cycle of heart action.

The device may be inserted into a heart valve in the first shape of the device and the device may change the shape of the heart valve by stretching the heart valve between the commissures. The stretching of the heart valve between the commissures implies that mid-portions of the leaflets are brought closer together. Thereby, the ability of the leaflets to close the heart valve properly is improved.

The invention provides a device that may be used in a simple manner for improving the function of a leaking heart valve. The device is arranged for accomplishing a change of the geometrical shape of the heart valve so as to improve the ability of the leaflets to close properly. Whereas known methods of changing the shape of the heart valve for treating a leaking valve have been focused at compressing the heart valve, the present invention provides a device to be used for stretching the heart valve in the direction of the heart valve opening. The invention is thus based on an insight that a leaking heart valve may be treated by accomplishing a change of the geometrical shape of the valve by stretching the valve in a certain direction instead of compressing the valve.

The device provides a first shape which is designed to fit the heart valve such that contact may be established between the device and two commissures of the heart valve. Therefore, the device presents a distance between two contact points that essentially correspond to a distance between the two commissures of the heart valve. The device need not be placed in contact exactly in the commissure, but may make contact with valve tissue in the proximity of the commissure. Therefore, the distance between the contact points of the device in the first shape of the device need not exactly correspond to the distance between the commissures. The device may be compressed or restrained to temporarily assume or present its first shape, whereby the device assumes its second shape when the restrain on the device is released. Alternatively, the device may be transferred between two predetermined shapes.

The device provided for accomplishing the geometrical shape change may be applied to the heart valve so as not to interfere with the blood flow through the heart valve. The device may be placed in abutment with heart valve tissue along substantially the entire length of the device. This implies that the device may over time grow into the valve tissue, whereby the device does not present any surface of foreign material that may cause blood clot forming. In order to grow into the valve tissue, the device may not need to initially abut valve tissue over its entire length. However, major parts of the device would need to abut valve tissue and parts which do not abut the valve tissue should be placed in close proximity to valve tissue such as to eventually grow into the valve tissue.

Further, the device is arranged to abut valve tissue throughout a cycle of heart action. This implies that the device, if grown into valve tissue, would not impair the movement of the leaflets during heart action.

There are several conceivable shapes of the device that fulfil the requirement of abutting valve tissue along substantially the entire length of the device throughout a cycle of heart action. A person skilled in the art will however understand that the device in its second shape should primarily abut valve tissue of the annulus or close to the annulus, since the movements of the heart valve are smallest there. Several different embodiments for achieving the abutment between the device and valve tissue will be presented below.

As used herein, the term "commissure" implies a site of junction between leaflets of a heart valve.

The device may be arranged for establishing contact with the heart valve such that a transfer from the first shape to the second shape accomplishes a change of shape of the heart valve. The device is therefore arranged for the heart valve to be attached or secured to the device so that the device, when transferring from the first shape to the second shape, will bring the heart valve with it to change the shape of the heart valve.

The device may further comprise fixating means for attaching the device to valve tissue. The fixating means may be arranged for attaching the device to valve tissue before the transfer of shapes of the device occurs. This fixes the valve tissue to the device, whereby the valve tissue will follow the shape change of the device.

The fixating means may be e.g. barbs or hooks arranged extending from the device so as to engage with valve tissue.

The fixating means may be arranged at the contact points of the device. This implies that the device may be attached to the commissures of the heart valve and that the Change of distance between the contact points will change the distance between the commissures.

The device may be hook-shaped at the contact points for providing the fixating means. These hooks may engage the both upper and lower sides of the leaflets at the commissures so as to hook on the device to the leaflets.

Alternatively, the device may comprise a portion arranged for receiving a fixating means for attaching the device to valve tissue. The device may be attached to valve tissue by means of e.g. clips or sutures.

The portion for receiving a fixating means may be arranged at the contact points of the device. This implies that the device may be attached to the commissures of the heart valve and that the change of distance between the contact points will change the distance between the commissures.

The device may have an elongate part between the first and second contact points. The form of an elongate part may easily be adapted to the form of the heart valve such that the elongate part may be arranged in abutment with valve tissue in the second shape of the device.

The elongate part may, in the second shape of the device, have a form that corresponds to at least a part of the annulus. Thus, the device may be arranged in the heart valve such that the elongate part abuts against a part of the annulus, which is stationary during a cycle of heart action.

The device may be angled at the contact point for enabling abutment with the valve tissue throughout a cycle of heart action. The contact point is to be placed in contact with a commissure of the heart valve, that is in the opening of the heart valve. Therefore, the device may need to be angled at the contact point for being placed in abutment with valve tissue between the contact points.

The elongate part in the second shape of the device may be C-formed. A device with such a form may abut valve tissue of the annulus or near the annulus when placed in the heart valve.

The elongate part of the device may have a wave-like form. This implies that the device may be compressed in the first shape by compressing the wave-like form of the device. The device may then present an elastic force pushing the device to assume its second shape by extending the wave-like form.

The device may be ring-formed. This implies that the device may be arranged in the heart valve to mainly engage the annulus or valve tissue in close proximity of the annulus.

The device may exhibit an inherent force for transferring the device from said first shape to said second shape. This implies that the device itself may provide the transfer of shapes when inserted to the heart valve.

The device may be formed to exhibit a spring force for transferring the device from said first shape to said second shape. Thus, the device may be compressed for bringing it to the first shape and will assume the second shape when a compressing force is released.

The device may be made of a shape memory material for providing the inherent force. The shape memory may be activated when the device has been inserted to the heart valve, e.g. by heating the device to a predetermined temperature.

The invention also provides a method for improving the function of a heart valve comprised of valve tissue including an annulus, leaflets and at least a first and a second commissure between adjacent leaflets. The method comprises inserting a device in a first shape into the heart valve establishing contact between a first contact point of the device and valve tissue at said first commissure and a second contact point of the device and valve tissue at said second commissure, causing a transfer of shape of the first device from said first shape to a second shape such that a distance between the first and second contact point of the device is increased and, consequently, a distance between the first and second commissures of the heart valve is increased, and arranging the device in its second shape in the heart valve such that it along substantially its entire length abuts the valve tissue throughout a cycle of heart action.

Thanks to the invention, a geometrical shape change of the heart valve is accomplished by stretching the distance between commissures of the heart valve. This implies that the opening in the heart valve between the commissures is stretched and that mid-portions of the leaflets are brought closer together, whereby the ability of the heart valve to close properly is improved.

The method may further comprise fixating the device in the contact points to the commissures. This implies that the device is attached to the commissures such that the transfer of shape of the device certainly will bring the valve tissue with it to cause the geometrical shape change of the heart valve.

The method may further comprise restraining the device in its first shape during the inserting of the device into the heart valve. This implies that the device is prohibited from assuming its second shape during inserting of the device. Hereby, the device is brought to the heart valve in the first shape in which the device fits between the commissures of the heart valve.

The causing of the transfer of shape of the device may comprise releasing a restrain on the device. The device may exhibit an inherent force, which will cause the transfer of shape when a restrain is released.

The causing of the transfer of shape of the device may comprise activating a shape memory of the device. When a shape memory is activated, the device will strive towards assuming its second shape. The shape memory may be activated by e.g. heating the device to a transition temperature.

BRIEF DESCRIPTION OF DRAWINGS

The invention will now be described in further detail by way of example under reference to the accompanying drawings, on which.

DETAILED DESCRIPTION OF A PREFERRED EMBODIMENT

Figure 1:
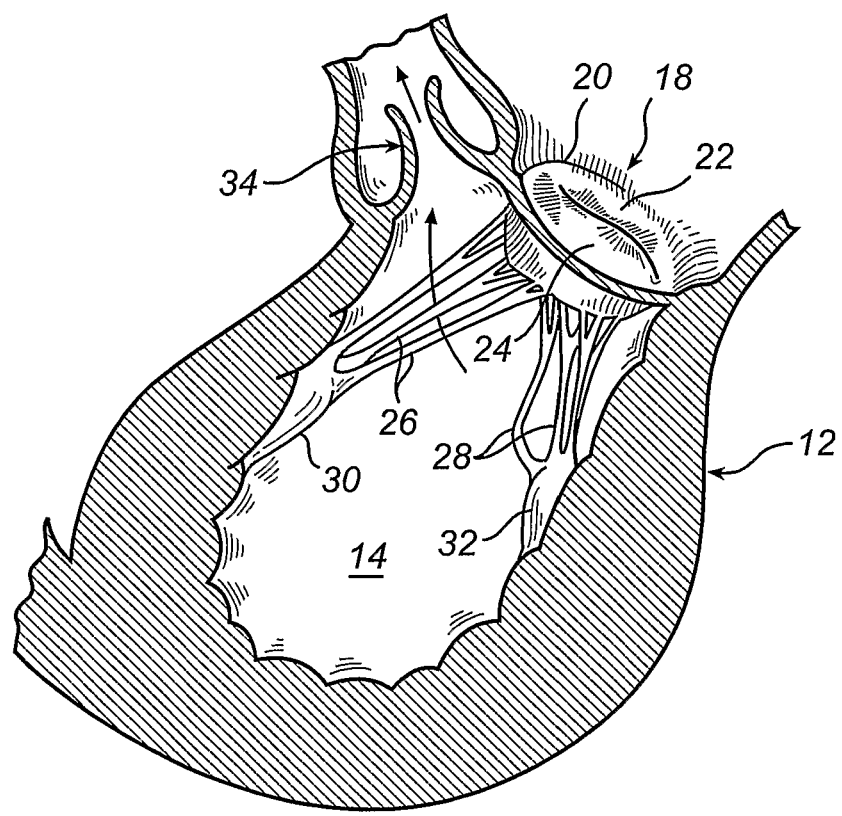
FIG. 1 is a schematical view of a cross section of the left ventricle of the heart.
Figures 2A, 2B:
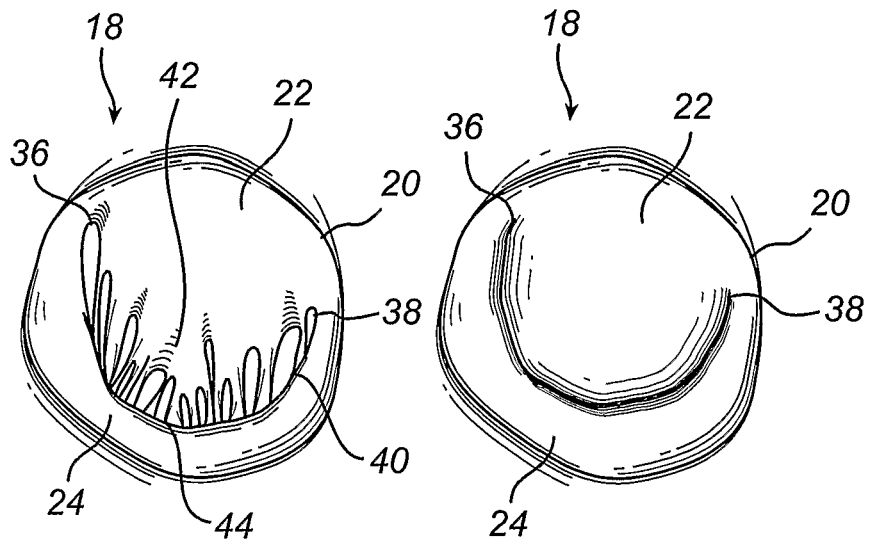
FIGS. 2A-2B are schematical views of a mitral valve of the heart shown in an open and closed state, respectively.

Referring now to FIGS. 1 through 2B, the function of the mitral valve 18 of the heart 12 will be described. The mitral valve 18 is situated between the left atrium and the left ventricle 14 of the heart. The mitral valve 18 includes an annulus 20 and a pair of leaflets 22, 24 which selectively allow and prevent blood flow into left ventricle 14. The leaflets 22, 24 are supported for coaptation by chordae tendinae or chords 26, 28 extending upwardly from respective papillary muscles 30, 32. Blood enters left ventricle 14 through mitral valve 18 and is expelled during subsequent contraction of heart 12 through aortic valve 34. As shown in FIG. 2A, the leaflets 22, 24 are drawn apart extending into the left ventricle 14 for opening the mitral valve 18 and allowing passage of blood into the left ventricle 14. As shown in FIG. 2B, the leaflets 22, 24 make contact to seal the mitral valve 18 in order to prevent blood transport from the left ventricle 14 back into the left atrium.

The mitral valve has an anterior leaflet 22 and a posterior leaflet 24. The leaflets 22, 24 are joined at commissures 36, 38 and the mitral valve 18 has an opening 40 between the commissures 36, 38. The anterior leaflet 22 is larger than the posterior leaflet 24, whereby the opening 40 of the mitral valve 18 has an arcuate shape. The opening 40 is opened and closed by movement of the leaflets 22, 24. The movement is mainly performed by free edges 42, 44 of the leaflets 22, 24 between the commissures 36, 38.

Figure 3:
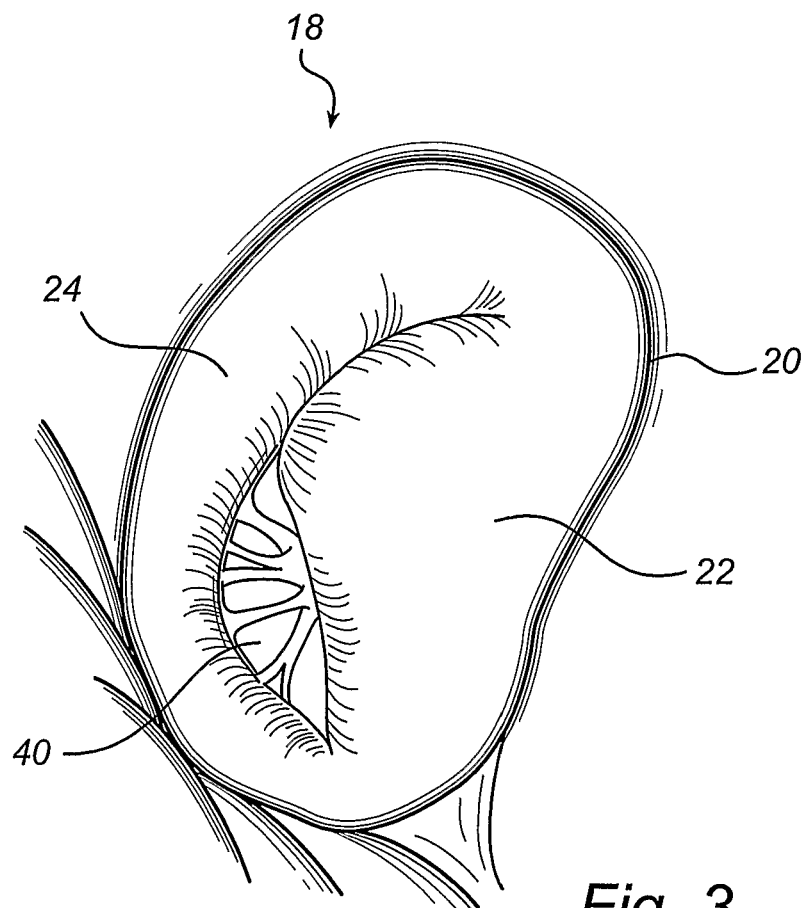
FIG. 3 is a schematical view of a diseased mitral valve.

In FIG. 3, a diseased mitral valve 18 is shown. The leaflets 22, 24 are not able to coapt properly, whereby the opening 40 in the valve 18 is not completely closed. Blood will now leak through the opening 40 backwards from the left ventricle 14 into the left atrium. This implies that the function of the heart 12 is reduced, since blood flows backwards through the system instead of being pumped out to the aorta. Therefore, there will be a need for ensuring that the leaflets 22, 24 are able to close the valve 18 properly.

Figure 4A:
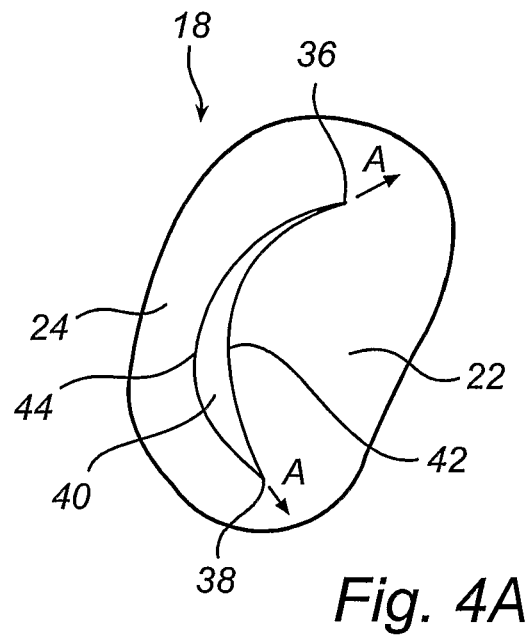
FIGS. 4A-4B are schematical views of the mitral valve indicating the shape of the mitral valve before and after being treated.
Figure 4B:
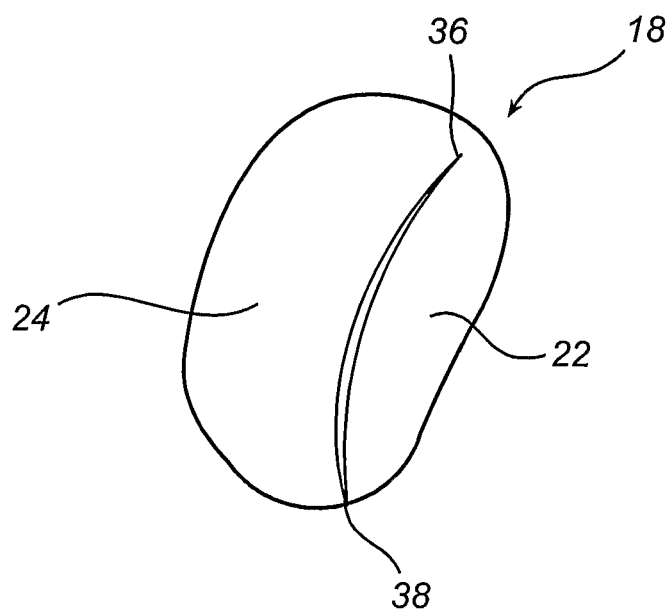

Referring now to FIGS. 4A-4B, the principle of treating a diseased mitral valve 18 with a device according to the invention will be described. FIG. 4A shows a mitral valve 18 with an opening 40 which has not been completely closed due to inability of the leaflets 22, 24 to coapt properly. Arrows A indicate a force to be applied to the valve 18 in order to remodel the valve 18 such that the leaflets 22, 24 are to be able to close properly. As shown in FIG. 4A, the valve is remodeled by drawing the commissures 36, 38, i.e. the sites of junction between the leaflets 22, 24, apart. This implies that the mitral valve opening 40 is stretched and that the free edges 42, 44 of the leaflets 22, 24 are brought closer together. Hereby, the leaflets 22, 24 are able to close the valve 18 preventing leakage.

Even though the description is made with regard to the mitral valve, it will be appreciated that the present invention is applicable to any other valve with two leaflets or to valves with three leaflets as well.

Referring now to FIGS. 5A-5G, embodiments of a device 50 according to the invention for treating a diseased mitral valve 18 will be described. The device is to be inserted in the mitral valve 18 to make contact with the commissures 36, 38. When contact is established between the device 50 and the commissures 36, 38, the device 50 will undergo a transfer of shape in order to bring the valve tissue with it and perform remodeling of the valve 18 as described above with reference to FIGS. 4A-4B.

As shown in FIGS. 5A-5G, the device 50 comprises a first contact point 52 and a second contact point 54, which are to make contact with valve tissue at the commissures 36, 38, respectively. The device 50 may be hook-shaped at the contact points 52, 54, whereby the device 50 may establish contact on both sides of the leaflets 22, 24 at the commissures 36, 38. The device 50 may at the contact points 52, 54 further comprise barbs or spikes or any pointed protrusion (not shown), which may penetrate into valve tissue for fixating the device 50 to the valve tissue. Alternatively, the device 50 may be arranged for being fixed by sutures or clips to the valve tissue.

When implanted, the entire device 50 should make contact with the valve tissue in order to enable the device 50 growing into the valve tissue. This implies that the device 50 will not exhibit a surface of foreign material to the blood flow and thereby blood clotting is prevented. To this end, the device 50 may have an elongate part 56, as shown in FIGS. 5A-5F, between the contact points 52, 54. The elongate part 56 may be arranged extending along valve tissue over its entire length, whereby the device 50 eventually may be fully grown into valve tissue. The device 50 should make contact with valve tissue throughout a cycle of heart action. Since the leaflets 22, 24 move during heart action for opening and closing the mitral valve 18, the elongate part 56 is preferably placed in contact with the annulus 20 or with leaflet tissue close to the annulus 20. The device 50 is bent at the contact points 52, 54 such that the elongate part may extend in a plane substantially perpendicular to a plane in which the hook-shape extend. This implies that the elongate part 56 of the device 50 may extend along valve tissue in a plane of the annulus 20 of the mitral valve 18 while the contact points 52, 54 are arranged in contact with the commissures 36, 38 of the mitral valve 18. Alternatively, the elongate part 56 may be fixed to contact portions of the device 50 such that the elongate part 56 may extend in the plane of the annulus 20.

Figure 5A:
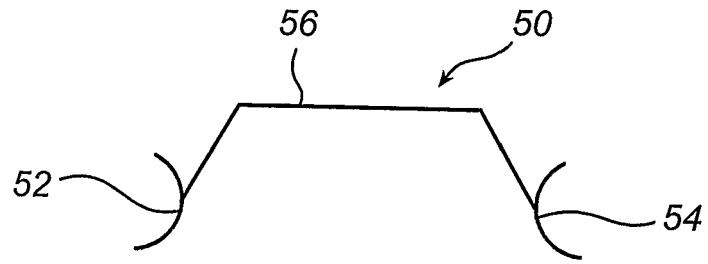
FIGS. 5A-5G are schematical views of different embodiments of a device according to the invention.
Figure 5B:
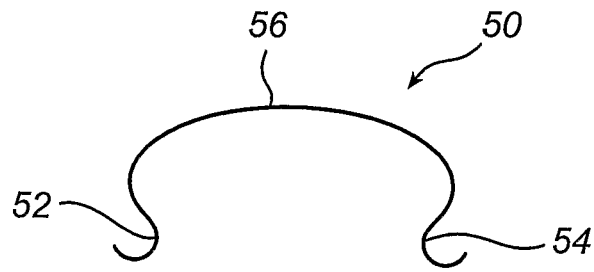
Figure 5C:
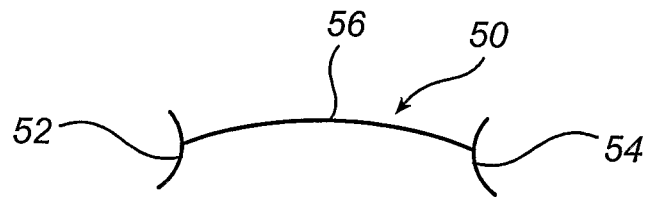
Figure 5D:
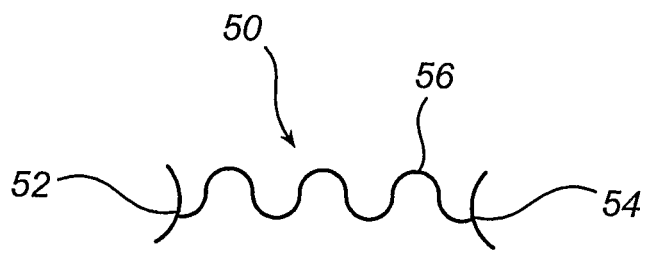
Figure 5E:
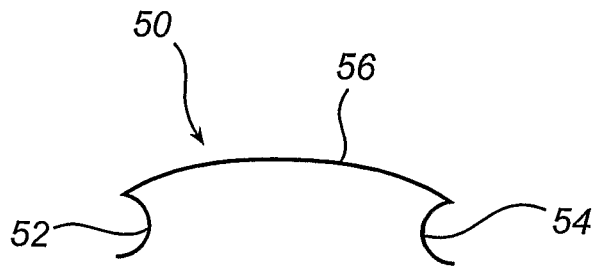
Figure 5F:
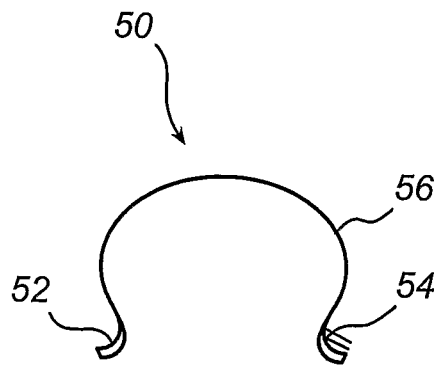

The elongate part 56 may extend in numerous different ways between the contact points 52, 54, as shown in FIGS. 5A-5F. The elongate part 56 is to be placed in contact with the valve tissue between the commissures 36, 38. As shown in FIGS. 2A through 4B, the opening 40 of the mitral valve 18 has an arcuate shape. Therefore, the elongate part 56 may be in contact with valve tissue even if it extends essentially along a straight line between the commissures 36, 38. However, if the elongate part 56 has an arcuate or curved shape, it may be placed in contact with valve tissue closer to the annulus 20, which tissue undergoes less movement during heart action. Therefore, the elongate part 56 may be bent as shown in FIG. 5A, C-shaped as shown in FIGS. 5B and 5F, or slightly arcuate as shown in FIGS. 5C and 5E. However, the elongate part may have a wave-like form as shown in FIG. 5D extending along the anterior leaflet 22 of the mitral valve 18.

Figure 5G:
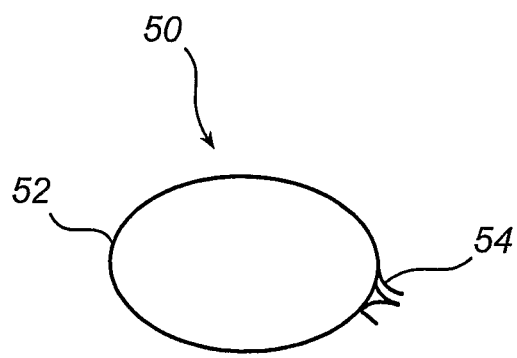

As shown in FIG. 5G, the device may alternatively be ring-formed to extend mainly along the annulus 20 of the mitral valve 18. The ring-form deviates from the shape of the annulus 20 at the commissures 36, 38 for allowing contact between the device 50 and the commissures 36, 38.

Figure 6A:
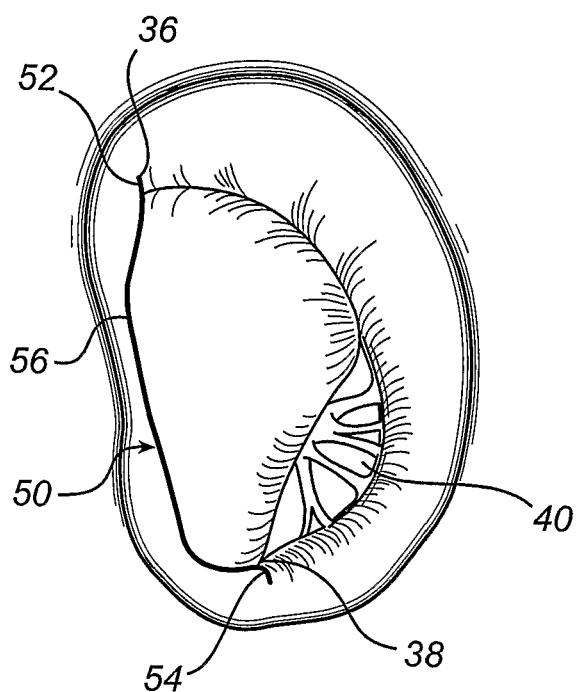
FIGS. 6A-6B are schematical views of a first embodiment of the device being applied to the mitral valve in a first and second shape of the device, respectively.
Figure 6B:
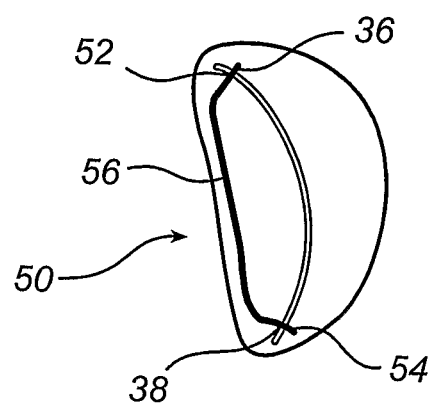
Figure 6C:
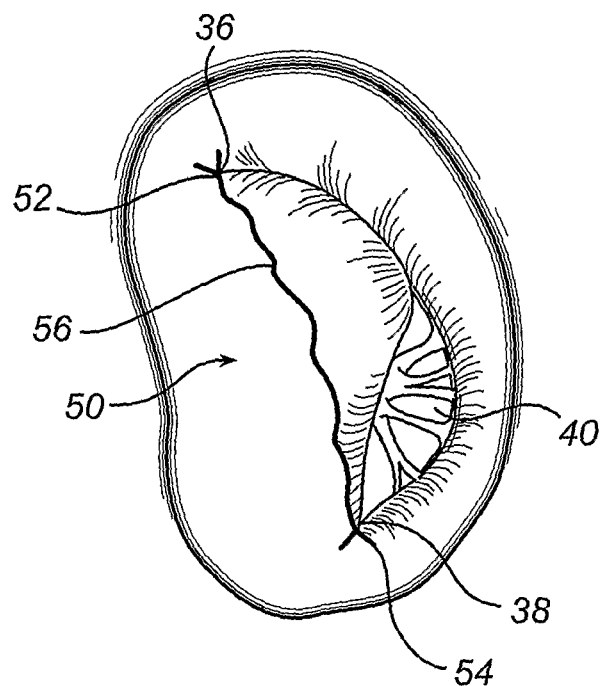
FIGS. 6C-6D are schematical views of a second embodiment of the device being applied to the mitral valve in a first and second shape of the device, respectively.
Figure 6D:
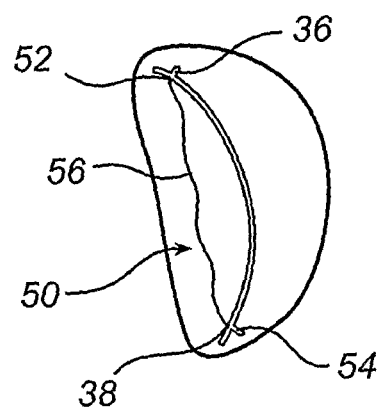

As shown in FIGS. 6A and 6C, the device 50 is inserted to the mitral valve 18 in a first shape. The device 50 is arranged in the first shape to establish the contact between the device 50 and the commissures 36, 38. The device 50 may then transfer to a second shape for remodeling the mitral valve 18, as shown in FIGS. 6B and 6D. The elongate part 56 changes form between the first and second shapes of the device 50. The elongate part 56 becomes less arcuate or curved in order to push the contact points 52, 54 further apart and thereby stretch the opening 40 of the mitral valve 18 such that the free edges 42, 44 of the leaflets 22, 24 are brought closer together.

Even though the device 50 is shown in FIGS. 6A-6D placed on the atrial side of the mitral valve 18, it should be understood that the device 50 may alternatively be placed on the ventricular side of the valve 18. The device 50 may then be placed in contact with the chords 26, 28 such that the device 50 abuts the ventricular side of the valve 18 and may grow into the valve tissue.

The device 50 may be resilient such that, when deformed into a first shape, it has an internal strive towards assuming the second shape. The device 50 may then be restrained by an outer force for keeping it in the first shape during insertion of the device 50 between the commissures 36, 38 of the heart valve. The restrain on the device 50 may be arranged to bend the elongate part 56 or compress the elongate part 56 such that the contact points 52, 54 are brought closer together. The device 50 may be made of a fairly rigid material, such that the resilience of the device 50 will restore the shape of the device 50 in order to remodel the mitral valve 18 when a restrain on the device 50 is released. However, the device 50 may be slightly flexible in its second shape to allow small movements of the annulus 20 and commissures 36, 38 during heart action while still keeping the commissures 36, 38 stretched apart in the remodeled shape. The device may be made of any suitable medical grade material(s), such as medical grade metals or plastics.

Alternatively, the device 50 may be made of a shape memory material. The device 50 may then be inserted into the mitral valve 18 in a martensitic state, wherein the device is relatively soft and may be easily deformed. Thus, the device 50 may in the martensitic state easily be inserted into contact with the commissures 36, 38 of the mitral valve 18. When the device is heated above a transition temperature, the device 50 transforms into an austenitic state and assumes a programmed shape. Thus, the device 50 has an inherent strive towards assuming the second shape and maintains its desired shape. The device may be made of a shape memory alloy, such as Nitinol, or a shape memory polymer.

Typically, the distance between the contact points of the device in its first shape is 18-20 mm, which corresponds to a normal distance between the commissures of the mitral valve. The transfer of shape of the device may typically create a 40% increase in the distance between the contact points for remodelling the mitral valve.

Figure 7:
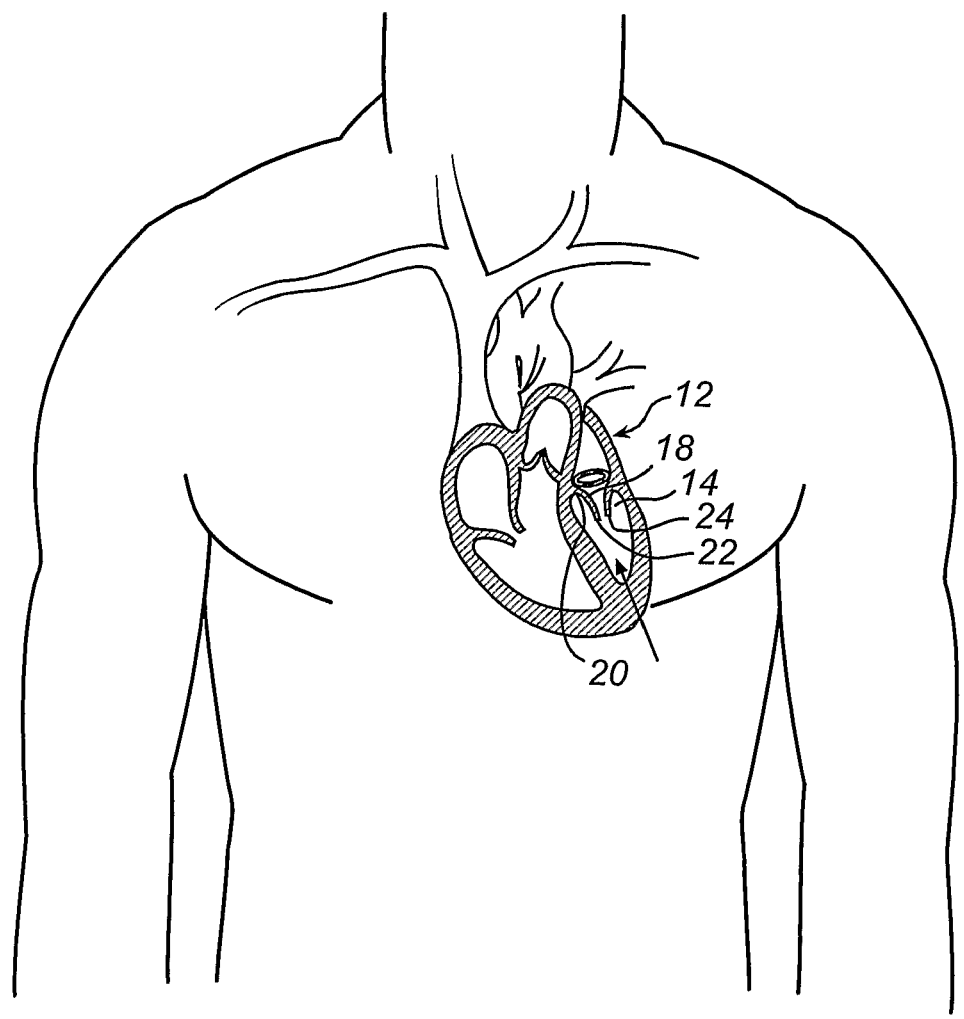
FIGS. 7, 8A-8B and 9A-9B are schematical views of a heart illustrating a method for applying a device according to the invention to the mitral valve.

A method for treating a heart valve by means of the device will now be described. The device may be implanted in the heart by means of open surgery. The device is brought into the mitral valve 18 and placed in contact with the commissures 36, 38. The device may be inserted to the mitral valve 18 through the apex of the heart 12, as illustrated in FIG. 7. The device 50 may during insertion be restrained in the first shape e.g. by pressing the elongate part 56 to bend the elongate part 56 or by a restrain wire extending between different portions of the elongate part 56 keeping these portions at a maximum distance from each other. Alternatively, the device 50 is held in its first shape by means of holding a temperature below a transition temperature for preventing the device 50 from assuming its second shape.

When the device 50 has been placed in contact with the commissures 36, 38, the device 50 is fixed to the valve tissue. This may be accomplished by attaching portions of the device 50 to the valve tissue by means of e.g. suturing or applying one or more clips to the device and valve tissue. Alternatively, fixating means are arranged on the device 50 and penetrate into valve tissue for fixing the device 50 to the valve tissue.

When the device 50 has been securely fixed to the valve tissue, the device 50 is allowed to transfer from its first to its second shape. Thus, a restrain is released by e.g. releasing a pressing force on the elongate part 56 or cutting a restrain wire. Alternatively, the device 50 may be heated for assuming an austenitic state and thereby transforming into its programmed, second shape. When assuming its second shape, the device 50 will cause a remodeling of the mitral valve 18 such that the opening 40 of the mitral valve 18 takes a form that may be properly closed by the leaflets 22, 24.

Referring now to FIGS. 8A-8B and 9A-9B, a catheter-based method for inserting the device 50 will be described.

Figure 8A:
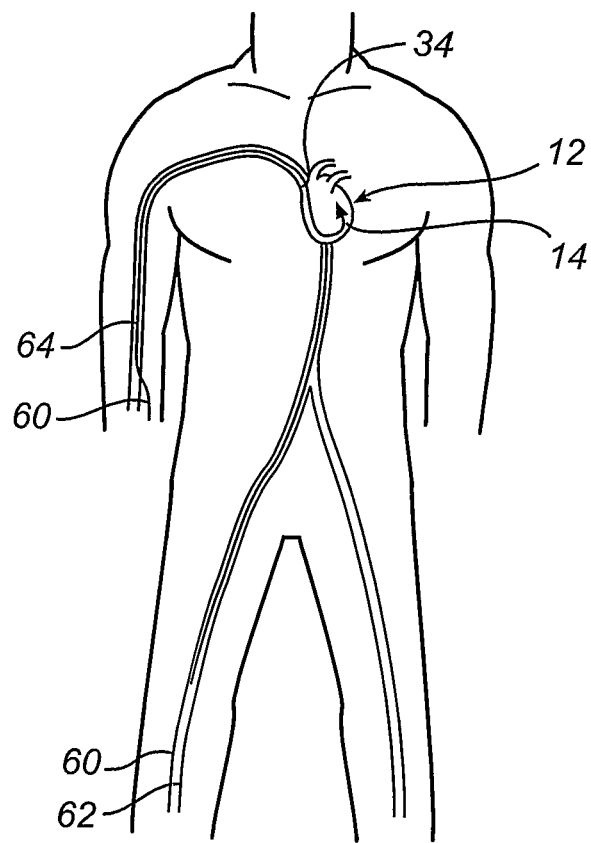
Figure 8B:
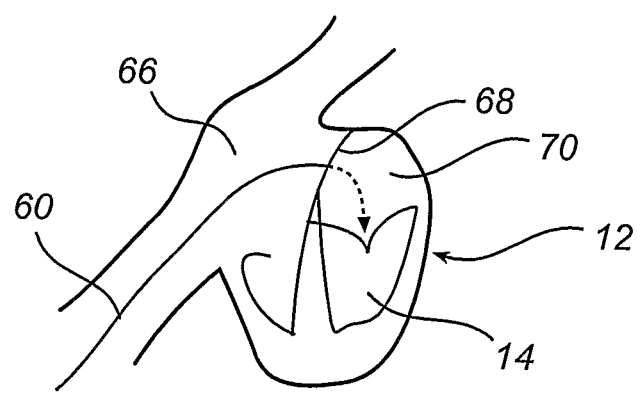

The device 50 is inserted by means of a catheter 60 into the heart 12. The catheter 60 is entered into the body through the femoral artery 62 in the groin or the subclavian artery 64 in the arm of the patient and is guided into the heart 12 retrograde through the artery and through the aortic valve 34 into the left ventricle 14, as shown in FIG. 8A. Alternatively, the catheter 60 may be guided through vena cava into the right atrium 66 and may penetrate the interatrial septum 68 to reach the left atrium 70, as shown in FIG. 8B.

Figure 9A:
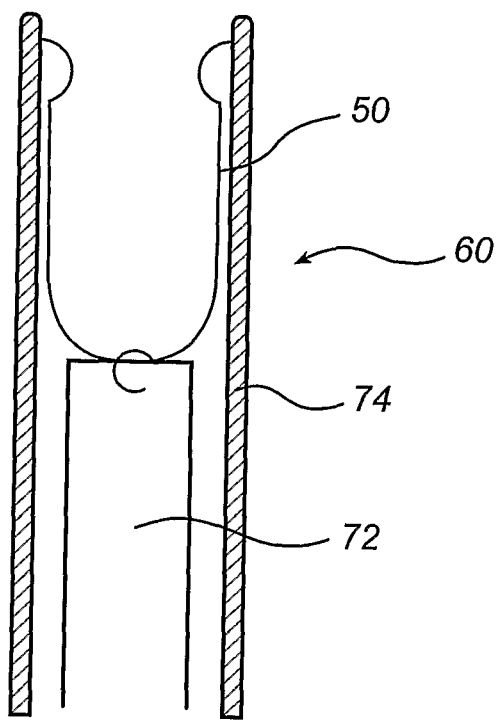
Figure 9B:
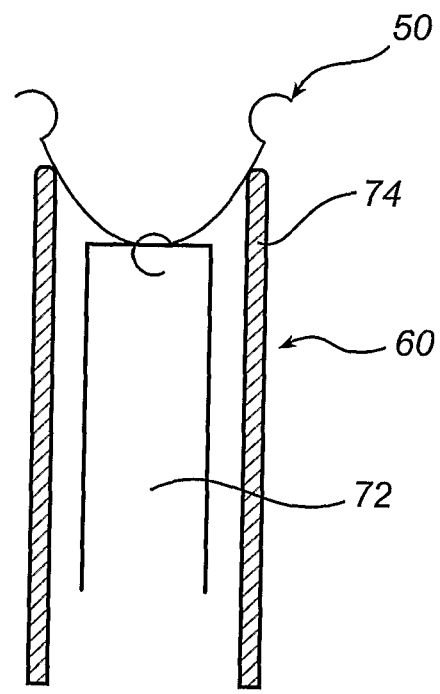

The device 50 may be arranged in the catheter 60 on a distal end of a carrier 72 and be covered by a restraining sheath 74, as shown in FIG. 9A. When the catheter 60 has been inserted to the mitral valve 18, the carrier 72 may be pushed partially out of the restraining sheath 74, as shown in FIG. 9B. Thus, the contact points 52, 54 of the device 50 may establish contact with the commissures 36, 38. Thereafter, the carrier 72 may be completely pushed out of the restraining sheath 74 for allowing the device 50 to assume its second shape and remodel the mitral valve 18. Then, the device 50 may be released from the carrier 72 and the catheter 60 may be withdrawn from the body leaving the device 50 in place in the mitral valve 18.

It should be emphasized that the embodiments described herein are in no way limiting and that many alternative embodiments are possible within the scope of protection defined by the appended claims.

What is claimed is:

1. A device for improving the function of a heart valve comprised of valve tissue including an annulus, leaflets and at least a first and a second commissure between adjacent leaflets,
    said device comprising an elongate part comprising a first contact point and a second contact point,
    said device having a first shape and a second shape,
    said first shape comprising a distance between the first contact point and the second contact point substantially corresponding to a distance between said first and second commissures of the heart valve
    said second shape comprising a distance between the first and the second contact points which is greater than said distance in the first shape,
    said device in said first shape being configured for insertion into the heart valve to establish a contact between the first contact point and valve tissue at the first commissure and to establish a contact between the second contact point and valve tissue at the second commissure,
    said device being movable from said first shape to said second shape after insertion into the heart valve, whereby the elongate part is less arcuate between the first contact point and the second contact point in the second shape in order to push the contact points and commissures further apart and stretch the opening of the heart valve and change the shape of the heart valve such that free edges of the leaflets are brought closer together in a remodeled shape,
    the entire length of the elongate part is configured to contact the valve tissue substantially in a plane of the annulus when the device is in the second shape, and
    said device, when in the second shape, extending along substantially its entire length between the first contact point and the second contact point in contact with the valve tissue throughout a cycle of heart action,
    said device comprising a portion arranged to receive a fixation device to attach the device to the valve tissue.

2. Device according to claim 1, wherein the fixation device comprises a suture.

3. Device according to claim 1, wherein the fixation device comprises a clip.

4. Device according to claim 1, wherein the portion arranged to receive the fixation device is arranged at the contact points.

5. Device according to claim 1, wherein the fixation device is arranged on the device and penetrates into valve tissue for attaching the device to the valve tissue and fix the device in the second shape.

6. Device according to claim 1, wherein the first and second contact points are hook-shaped.

7. Device according to claim 1, comprising protrusions at the contact points for penetrating into the valve tissue and fixate the device.

8. Device according to claim 1, comprising barbs or spikes at the contact points for penetrating into the valve tissue and fixate the device.

9. The device according to claim 1, wherein the elongate part, in the second shape, has a form that corresponds to at least a part of the annulus.

10. The device according to claim 1, wherein the elongate part has an arcuate or curved shape.

11. The device according to claim 1, wherein the device is ring-formed to extend mainly along the annulus of the heart valve.

12. The device according to claim 11, wherein the ring-form deviates from the shape of the annulus at the commissures for allowing contact between the device and the commissures.

13. The device according to claim 1, wherein the elongate part extend along the valve tissue in a plane of the annulus while the first and second contact points are arranged in contact with the first and second commissures.

14. The device according to claim 1, wherein device is configured to be placed in contact with the chordae of the heart valve such that the device abuts a ventricular side of the heart valve.

15. The device according to claim 1, wherein the device is resilient such that, when deformed into the first shape, it has an internal strive towards assuming the second shape.

16. The device according to claim 1, wherein the device is flexible in its second shape to allow movements of the annulus and commissures during heart action while still keeping the commissures stretched apart in the remodeled shape.

17. The device according to claim 1, comprising a shape-memory material, whereby, when the device is heated above a transition temperature, device transforms into an austenitic state and assumes the second shape as a programmed shape.

18. The device according to claim 17, wherein the device is made of a shape memory alloy, such as Nitinol, or a shape memory polymer.

19. The device according to claim 1, wherein the transfer of the shape of the device from the first shape to the second shape creates a 40% increase in the distance between the contact points for remodelling the mitral valve.

20. The device according to claim 1, comprising a restraining wire extending between portions of the elongate part keeping these portions at a maximum distance from each other in the first shape.

* * * * *